US00PP26014P3

(12) United States Plant Patent
Olesen

(10) Patent No.: US PP26,014 P3
(45) Date of Patent: Oct. 27, 2015

(54) SHRUB ROSE PLANT NAMED 'POULREN022'

(50) Latin Name: ***Rosa* hybrid**
Varietal Denomination: Poulren022

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 172 days.

(21) Appl. No.: 13/986,940

(22) Filed: Jun. 14, 2013

(65) Prior Publication Data

US 2014/0373223 P1 Dec. 18, 2014

(51) Int. Cl.
*A01H 5/02* (2006.01)

(52) U.S. Cl.
USPC ..... Plt./107

(58) Field of Classification Search
USPC ..... Plt./107, 150, 138
CPC ..... A01H 5/0222; A01H 5/0216; A01H 5/00; A01H 5/02
See application file for complete search history.

(56) References Cited

PUBLICATIONS

Poulsen Roser A/S Naomi retrieved on Jan. 14, 2015, retrieved from the Internet <www.poulsenroser.com/assortment/rose-collections/renaissance/naomi.aspx> one page.*
Upov Pluto Plant Variety Database 20150114 for *Rosa* 'Poulren022', retrieved on Jan. 14, 2015, retrieved from the Internet <www3.wipo.int/pluto/user/en/index.jsp> one page.*
Viveros Guzman Agosto 2010 pp. 1-73.*

* cited by examiner

*Primary Examiner* — June Hwu

(57) ABSTRACT

A new garden rose plant of the grandiflora class which has abundant, deep pink flowers and attractive foliage. This new and distinct variety has shown to be uniform and stable in the resulting generations from asexual propagation.

1 Drawing Sheet

Botanical designation: *Rosa* hybrid.

Variety denomination: Shrub Rose Plant Named 'Poulren022'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poulren022', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant, large, deep pink flowers with strong fragrance;
2. Vigorous, but compact growth when propagated both as a budded rose and on its own roots; and
3. Exceptional disease resistance.

This combination of qualities is not present in previously available commercial cultivars of this type, known to the inventor, and distinguish 'Poulren022' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulren022' was selected in the spring of 2004 by the inventor as a single plant from the progeny of the aforementioned hybridization.

Asexual reproduction of 'Poulren022' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulren022' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulren022'. Specifically illustrated in the drawing are flowers at various stages of development, flower in parts, leaves, and stems.

DETAILED DESCRIPTION OF THE VARIETY

The following is a description of 'Poulren022',as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Ausbord', U.S. Plant Pat. No. 7,220 are compared to 'Poulren022' in Chart 1.

CHART 1

| | 'Poulren022' | 'Ausboard' |
|---|---|---|
| Flower | Strong Pink, Very Fragrant | Strong Pink, Very Fragrant |
| Flower Diameter | 8 cm | 11 cm |
| Plant Height | 75 cm | 120-150 cm |

Flower and Flower Bud

Blooming habit: Continuous.

Flower bud:

*Size*.—Upon opening, 25 mm in length from base of receptacle to end of bud. Bud diameter is 20 mm.

*Bud form*.—Urceolate.

*Bud color*.—As sepals divide Red Group 53B.

*Sepal inner surface*.—Color: Green Group 138C with moderate anthocyanin the color of Greyed-Red Group 182A. Surface: Smooth, moderate pubescence.

*Sepal outer surface*.—Color: Yellow-Green Group 144A with strong anthocyanin the color of Greyed-Purple Group 185A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—30 mm long by 13 mm wide.

*Receptacle*.—Texture: Smooth. Size: 10 mm in height by 11 mm wide. Color: Yellow-Green Group 144A. Anthocyanic pigments the color of Greyed-Purple Group 185A observed. Shape: Campanulate.

*Pedicel*.—Surface: Smooth. Length: 55 mm. Diameter: 4 mm on average. Color: Yellow-Green Group 144B. Strong anthocyanic pigments the color of Greyed-Purple Group 183B observed. Strength: Strong.

*Peduncle*.—Length: 1 to 5 cm. Diameter: 3 to 4 mm. Color: Yellow-Green Group 144B. Strong anthocyanin the color of Greyed-Purple Group 183B.

Flower bud development: Flower buds are borne in clusters of 3 to 5 flower buds per stem, resembling a corymb.

Flower bloom:

*Fragrance*.—Strong perfume.

*Duration*.—The blooms have a duration on the plant of approximately 14 days. Petals fall cleanly away from plant after flowers have fully matured.

*Size*.—Flower diameter is 80 mm when open. Flower depth is 50 mm.

*Flower shape*.—General shape is a quartered-rosette, very double, with many overlapping petals packed into quarter sections.

*Shape of flower, side view*.—The upper portion is flat. The lower portion is concave.

Petalage: Very Double. Under normal conditions, flowers have 75 petals total, 10 of which are petaloids.

General tonality of flower: Open flowers are Red-Purple Group N66B. No changes in tonality as the flower matures.

Petal color:

*Upon opening, outer petals*.—Upper surface: Red-Purple Group N66B. Lower surface: Red-Purple Group 67B at the middle and marginal zone. At the basal zone Red-Purple Group 58B. Variegation: Occasional streaks of White Group 155A on upper and lower surfaces.

*Upon opening, inner petals*.—Upper surface: Red-Purple Group N57A. Lower surface: Red-Purple Group 58B. Variegation: Occasional streaks of White Group 155A on upper and lower surfaces.

*Basal petal spots, upon opening*.—Upper surface: Yellow Group 2C. Lower surface: Yellow Group 2C.

*After opening, outer and inner petals*.—Upper surface: Red-Purple Group N57B. Lower surface: Red-Purple Group 67B. Variegation: Occasional streaks of White Group 155A on upper and lower surfaces.

*Basal petal spots, after opening*.—Upper surface: Yellow Group 4D. Lower surface: Yellow Group 4D.

Petals:

*Petal reflex*.—Medium.

*Margin*.—Entire and uniform. Medium to strong undulations of margin observed.

*Shape*.—Generally rounded. Apex shape: Rounded. Base shape: Rounded.

*Size*.—50 mm (l) by 50 mm (w).

*Texture*.—Smooth.

*Thickness*.—Average.

Petaloids:

*Size*.—25 mm (l) by 11 mm (w).

*Quantity*.—10 on average.

*Shape*.—Asymmetric. Base is acute. Apex is rounded.

*Color*.—Upper surface is Red-Purple Group N66B with some streaks of Yellow Group 4D. Lower surface is Red-Purple Group 67B.

Reproductive organs:

*Pollen*.—None observed.

*Anthers*.—Size: 3 mm in length. Color: Yellow Group 11B. Quantity: 35 on average.

*Filaments*.—Color: Red Group 55C. Length: 12 mm.

*Pistils*.—Length: 7 mm. Quantity: 45 on average.

*Stigmas*.—Color: White Group N155C.

*Styles*.—Color: Red Group 50B.

*Location of stigmas*.—Inferior in location relative to the length of the filaments and the height of the anthers.

*Hips*.—None Observed.

Plant

Plant growth: Upright, bushy. Plants are 75 cm in height, and 75 cm wide.

Stems:

*Color*.—Juvenile growth: Yellow-Green Group 144A with anthocyanin the color of Greyed-Red Group 178A. Mature growth: Yellow-Green Group 146B.

*Length*.—On average, canes are 50 cm from the base of the plant to the flowering portion.

*Diameter*.—7 mm.

*Internodes*.—On mature canes, there is an average distance of 40 mm between nodes.

*Surface texture*.—Young wood: Smooth. Older wood: Smooth.

Long prickles:

*Incidence*.—8 prickles per 10 cm of stem.

*Size*.—Average length of prickles on mature stems is 6 mm.

*Shape*.—Upper portion is linear. Lower portion is deep concave.

*Color*.—Juvenile prickles: Greyed-Purple Group 187B. Mature prickles: Greyed-Purple Group 187A.

Plant foliage:

*Compound leaf*.—160 mm (l)×120 (w).

*Quantity*.—2 leaves per 10 cm of stem on average.

*Leaf bearing angle to the stem*.—60 degrees.

*Color of juvenile foliage*.—Upper side: Yellow-Green Group 152C. Lower side: Yellow-Green Group N144A. Anthocyanin: Strong, Greyed-Red Group 180A.

*Color of mature foliage*.—Upper side: Yellow-Green Group 147A. Lower side: Yellow-Green Group 147B.

Plant leaves and leaflets:

*Stipules*.—Size: 12 mm in length. Quantity: 2 per compound leaf. Shape: Linear, slightly broad based with outward extending apecies. Margins: Finely serrated. Color: Green Group 143B.

*Petiole*.—Length: 25 mm. Diameter: 2 mm.

*Upper surface*.—Color: Yellow Group 144B with anthocyanic pigments the color of Greyed-Red Group 178A.

*Lower surface*.—Color: Yellow-Green Group 144B. Observations: Few small prickles observed.

*Rachis*.—Length: 70 mm. Upper surface: Color: Yellow Group 144B with anthocyanic pigments the color of Greyed-Red Group 178A.

*Lower surface*.—Color: Yellow-Green Group 144B. Observations: Few small prickles observed.

*Leaflet*.—Quantity: Normal number of leaflets leaves in middle of the stem is 7 leaflets. Margins: Serrated. Size: Average size of the terminal leaflet on normal leaves is 70 mm in length by 50 mm wide. Shape: Generally ovate. Base: Rounded. Apex: Cuspidate. Texture: Smooth. Thickness: Average. Arrangement: Odd pinnate. Venation: Reticulate. Glossiness: Very glossy.

Disease resistance: Above average resistance to powdery and downy mildew, rust, black spot, and botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Grandiflora rose class named 'Poulren022', substantially as illustrated and described herein, due to its abundant deep pink flowers, disease resistance, and extended period of bloom.

* * * * *

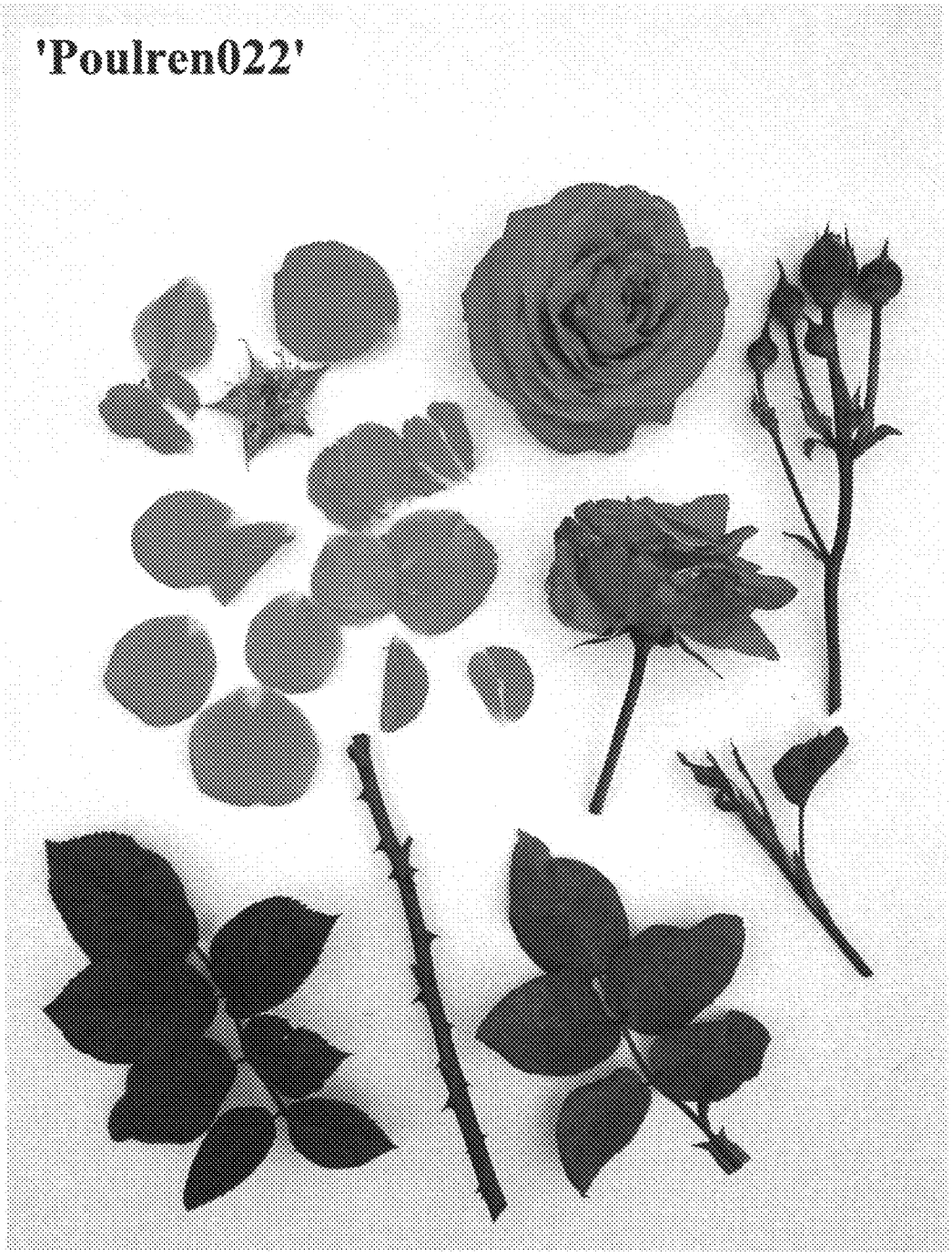
'Poulren022'